United States Patent [19]

Spagna et al.

[11] Patent Number: 5,798,641
[45] Date of Patent: Aug. 25, 1998

[54] TORQUE MAGNETOMETER UTILIZING INTEGRATED PIEZORESISTIVE LEVERS

[75] Inventors: Stefano Spagna, La Jolla; Michael Bancroft Simmonds, Del Mar, both of Calif.

[73] Assignee: Quantum Design, Inc., San Diego, Calif.

[21] Appl. No.: 819,376

[22] Filed: Mar. 17, 1997

[51] Int. Cl.$^6$ .......................... G01R 33/12; G01R 33/02; G01N 27/72; G01L 1/18
[52] U.S. Cl. .................... 324/228; 73/862.338; 324/226; 324/259; 324/261; 324/262
[58] Field of Search .............................. 324/201, 228, 324/235, 244, 249, 252, 259, 260, 261, 262, 226; 73/727, 514.21, 514.23, 514.29, 514.33, 514.34, 514.36, 862.338, 862.634

[56] References Cited

U.S. PATENT DOCUMENTS 5,107,708  4/1992  Seipler et al. ....................... 73/514.33
5,182,515  1/1993  Okada ................................. 324/259
5,542,297  8/1996  Mizuno ......................... 73/514.33 X

OTHER PUBLICATIONS

Tortonese et al., *Atomic Resolution With An Atomic Force Microscope Using Piezoresistive Detection*, Appl. Phys. Lett. 62(8), pp. 834–836 (1993).
Rossel et al., *Active Microlevers as Miniature Torque Magnetometers*, J. Appl. Phys., vol. 79, p. 8166 et seq. (1996).
Bauer et al., *Miniature Torque Magnetometer*, IBM Technical Disclosure Bulletin, vol. 38, No. 12, pp. 151, 152 (1995).

*Primary Examiner*—Gerard R. Strecker
*Attorney, Agent, or Firm*—Baker & Maxham

[57] ABSTRACT

A torque magnetometer employing integrated piezoresistive levers to measure magnetization of very small anisotropic samples. A sample holding platform is cantilevered from the substrate by parallel legs on which piezoresistors have been applied. A Wheatstone bridge, which includes the piezoresistors, is completely integrated on a magnetometer substrate. Specific output connections are made to the electrical conductors of the bridge in a manner to eliminate Hall effect error signals in an alternative embodiment.

27 Claims, 5 Drawing Sheets

TORQUE MAGNETOMETER UTILIZING INTEGRATED PIEZORESISTIVE LEVERS

BACKGROUND

1. Field of the Invention

The invention relates generally to sensitive magnetic measurements and more specifically to a system for measuring very small anisotropic samples (e.g., single crystals, thin films, among others) by means of an improved piezoresistive technique.

2. Description of the Related Art

Several types of sensitive torquemeters have been proposed over the years and successfully used for measurements of magnetic moments of metallic multilayers, high-Tc superconductors (in bulk and thin film form) and magnetic materials. The most advanced versions are capacitance torquemeters, in which a flexible beam holding the sample is symmetrically positioned between two capacitors plates. When used in conjunction with a variable magnetic field test chamber, the deflection of the capacitance torquemeter beam holding the sample produced by the magnetic torque $\tau = m \times B$ created by an applied magnetic field gives a measure of the intrinsic magnetic moment of the sample. In this equation, m is the sample moment and B is the applied field.

The first application of piezoresistive cantilevers was proposed for atomic force microscopy (AFM) by Tortonese et al., *Atomic Resolution With An Atomic Force Microscope Using Piezoresistive Detection*, Appl. Phys. Lett. 62, p. 834 (1993). Magnetometers of this type have since been commercialized by Park Scientific Instruments. Rossel et al., described in an article: *Active Microlevers as Miniature Torque Magnetometers*, J. Appl. Phys., Vol. 79, p. 8166 et seq. (1996), the use of these commercially available piezoresistive cantilevers for the first time as torque magnetometers in conjunction with a variable temperature and magnetic field test chamber used to study the physical properties of high Tc superconductors. By depositing a sample directly on a microlever Rossel and collaborators were able to measure the change in resistance of two piezoresistance elements confined in a region of high stress in the lever. The change in resistance of the piezoelements due either to bending or flexion is produced by the magnetic torque $\tau = m \times B$ and gives a measure of the intrinsic magnetic moment of the sample. In the prior art piezoresistance changes were measured by a remote detection circuit (outside the test chamber) connected in what is known as a Wheatstone bridge configuration. In this configuration, the resistance of the piezoresistive elements is measured and closely matched by two other resistances outside the test chamber. Any change in resistance of the piezoresistive elements due to the bending or flexion of the lever can then be detected by a voltmeter connected across the bridge. This gives a direct measure of the magnetic torque and hence the intrinsic sample moment.

While the apparatus worked well for many purposes achieving a torque sensitivity of approximately $10^{-14}$ Newton-meter (Nm), the extreme smallness of the levers [with typical dimensions of: length 165 micrometers (µm), width 90 µm and thickness of 4 µm] and open geometry of the design made the sample mounting extremely difficult and the exposed lever susceptible to breaking. Furthermore, use of this device was limited to extremely small size samples (less than one microgram with typical sample size of 30×30×10 µm).

Additional drawbacks of the known design which limited its commercial usefulness resulted from the fact that it employed a split detection circuit (which, as explained above, was partly outside the test chamber), causing unwanted imbalance in the measurement electronics due to the fact that a portion of the Wheatstone bridge (that is, the piezoresistive elements) was frequently subjected in the test chamber to very large magnetic fields and temperature variations. Typically, the imbalance of the piezoresistors with respect to the reference resistors (effectively shielded from any environmental change in temperature and magnetic field) in the bridge measurement electronics could be caused by spurious temperature dependent contact resistance from one of the wire bonds normally used to connect piezoresistive elements and complete the Wheatstone bridge. Other sources of possible output in accuracies in this Prior Art detection configuration is a gain variation (that is, a change in sensitivity) in the bridge as the piezoresistors' sensitivity and characteristics changed as functions of temperature and magnetic field. In particular, a spurious 1% change in resistance of the piezoresistive elements was observed (even with no sample) when the magnetic field was ramped to 5 Tesla (T). These background errors were extremely difficult to distinguish from a sample signal in a typical experiment.

In an attempt to eliminate the influence of these substantial problems upon sensitive measurements an extension of the prior art suggested by Rossel and collaborators was to perform a differential measurement with two identical cantilevers integrated with the Wheatstone bridge on the same chip. [Bauer et al., *Miniature Torque Magnetometer*, IBM Technical Disclosure Bulletin, Vol. 38, No. 12, pp. 151, 152 (1995)] However, several difficulties were immediately apparent in this extension of the original design. The first difficulty that one encounters is the practical complexity of electrically producing four independent active piezoresistors (that is, all bending or flexing as they would be on the two independent levers) integrated in a Wheatstone bridge configuration with identical sensitivities and responses to produce the good bridge balance needed for sensitive measurements. A second problem is the difficulty of fabricating two independent levers on the same chip with identical mechanical characteristics (that is, mechanical response to deflection or flexion) as is needed for a good differential measurement. This problem is (greatly amplified when attempting to build larger size levers for commercial use. While becoming greatly impractical to handle a chip with two identical levers of greater dimensions (on the order of a few millimeters) would be extremely difficult to fabricate to the precision needed for the measurement with standard photolothographic and etching techniques normally employed to produce the levers.

SUMMARY OF THE INVENTION

The primary purpose of the present invention is provide a highly sensitive magnetic sensor which enables measurement of the magnetic properties of very small anisotropic samples (e.g., single crystals, thin films, etc.). The invention incorporates a highly integrated torque-lever chip, preferably made from silicon wafers, for performing magnetic measurements by means of the magnetic torque $\tau = m \times B$, with the necessary detection circuitry needed for the measurements. The invention is directed to an apparatus and specific method of fabrication for a closed geometry (e.g., in-board from the perimeter of the chip of dimension 6×6×0.5 mm) torque-lever offering improved protection of the torque-lever during sample mounting (typically up to few tenths of a gram with maximum dimensions of 1.5×1.5×1.5 mm) and ease of handling for mounting of the torquemeter into any test apparatus with a nominal 9 mm bore normally used for subjecting the sample to variable temperature and magnetic field environment.

Other advantages of the present design include the ability of using the torque lever chip as a "stand alone" cartridge which can be easily mounted and electrically connected, using simple pressure contacts, to a wide range of attachments normally used in experimentation. For example, the compact size of the chip enables users to mount it into an evaporation chamber and deposit thin film samples (under ultra high vacuum conditions, for example, and at high temperature up to 400° C.) directly onto the lever surface. Characterization of these samples can then subsequently be performed in a separate test chamber equipped with variable temperature and magnetic field environments providing a background free magnetic measurement of the sample. The small size of the torque lever chip allows it to be best utilized by readily mounting it on a rotation platform for angular dependent torque measurements to be taken in the test chamber.

In the present invention the flexion of the lever is preferably detected as a measure of the magnetic torque because of its immunity to gravitational effects. The flexion, produced by the torque $\tau$, is measured to a high degree of sensitivity by the change in piezoresistance $\Delta R$. Appropriate detection means may be used to obtain signals representing resistance levels and changes, and the signals from the piezoresistors can be processed as needed by appropriate means. A simple but elegant signal detecting and processing means is an improved Wheatstone bridge configuration which is directly integrated on the torquemeter chip for superior balance and stability. This invention, in its preferred embodiment, uses two all-metallic piezoresistor traces (as opposed to silicon-doped p-type piezoresistors) of constantan in order to diminish temperature dependence of the circuit which could ultimately affect the sensitivity of the sensor. The balancing resistors of the bridge are also made of constantan to help balance out temperature variations. The unprecedented integration of the magnetic sensor with the detection electronics of this invention enables the user to eliminate the effects of contact resistance between the chip and its holder as well as to eliminate the errors caused by resistance changes in the bridge resistors due to magnetic fields and temperature.

When the Wheatstone bridge elements and connection traces are applied in a normal configuration, but now integrated onto the chip lever in accordance with the invention, spurious signals affecting the precision of the torque meter readings may occur at high magnetic fields (>1T) resulting from Hall effect voltages. As the applied magnetic field increases, the deleterious Hall effect voltages also increase. The errors resulting from Hall effect voltages can relatively large because the thickness of the wiring traces is small, compared with their width. This is the case when thin film techniques such as sputtering or evaporation are used to fabricate the Wheatstone circuit elements and connecting traces. As an alternative embodiment and an improvement on the basic invention, it has been found that the Hall effect problem can be eliminated by employing an alternative topology in configuring the bridge circuit. The key feature is that the bridge voltage is sensed from the inside of the bridge loop rather then outside. This causes the two voltage sensing points to be at equivalent voltage levels with regard to the development of Hall effect voltages. Thus there is no potential difference to generate this effect. This feature can be important in the design of the present torque magnetometer, since the bridge will often have very large varying magnetic fields applied to it or will be rotated in large magnetic fields.

In such circumstances, the Hall effect would create significant error signals which could be difficult to distinguish from the signal being generated due to the measurement sample.

BRIEF DESCRIPTION OF THE DRAWING

The objects, advantages and features of the invention will be more readily understood from the following detailed description, when read in conjunction with the accompanying drawing, wherein.

DETAILED DESCRIPTION OF THE PREFERRED EMBODIMENTS

Figure 1:
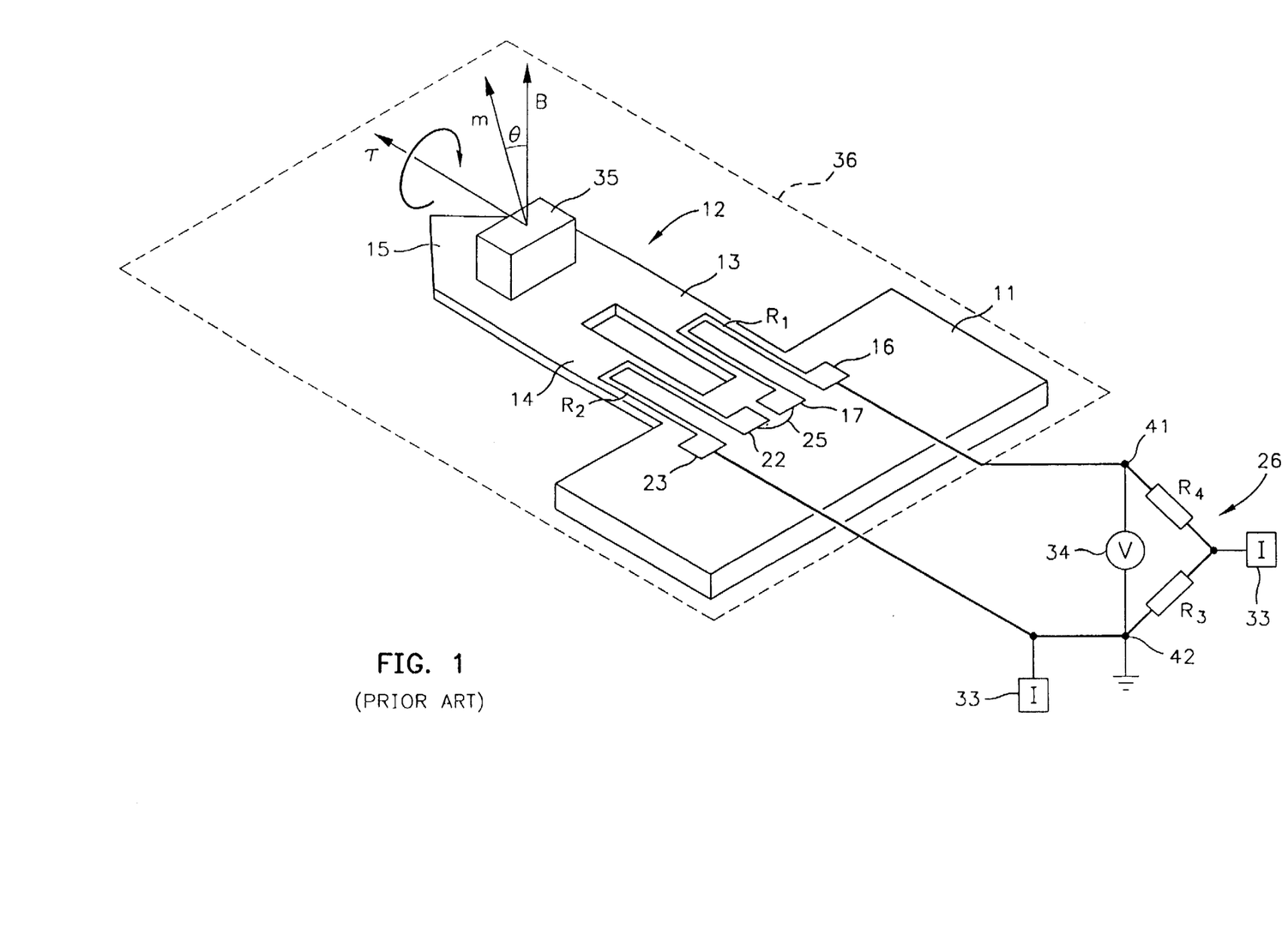
FIG. 1 is an isometric schematic view of a prior art torque lever chip with a remote Wheatstone bridge used for the detection electronics.

With reference now to the drawing and more particularly to FIG. 1 thereof, the prior art structure of a torque magnetometer is shown connected to non-conducting silicon substrate 11. The torque magnetometer is cantilevered flexible beam or microlever 12 formed with legs 13 and 14 and sample holding paddle or platform 15. On substrate 11 are electrical contact or bonding pads 16 and 17 connected to piezoresistor $R_1$, and bonding pads 22 and 23 connected to piezoresistor $R_2$. Pads 17 and 22 are connected together by conductor 25. Located external to substrate 11 is the rest of the Wheatstone bridge 26 comprised of balancing resistors $R_3$ and $R_4$, signal or power injections means 33, and output signal pickup 34, normally a detector to sense unbalanced bridge voltage.

When a test is to be made, a sample or specimen, such as small magnetic crystal 35, is mounted on platform 15 which is connected to substrate 11. Both the platform and the substrate are mounted; within the test chamber, which is represented generally by dashed lines 36. A magnetic field B is applied to the specimen in a conventional manner, possibly as taught by Rossel et al. The field results in a moment m on the specimen and a torque $\tau$ on the microlever. It is the torque that is the source of the signals from the piezoresistors which unbalance the bridge and provide an output signal between terminals 41 and 42 of the bridge.

The resistance of piezoresistive elements $R_1$ and $R_2$ is measured and closely matched with external resistors $R_3$ and $R_4$ to balance bridge 26. Any change in the sensing resistance elements $\Delta R_1$ and $\Delta R_2$ due to bending or flexion of the microlever is detected by voltmeter 34, providing a signal directly indicative of the magnetic torque on the microlever and hence the intrinsic moment of the sample.

Figure 2:
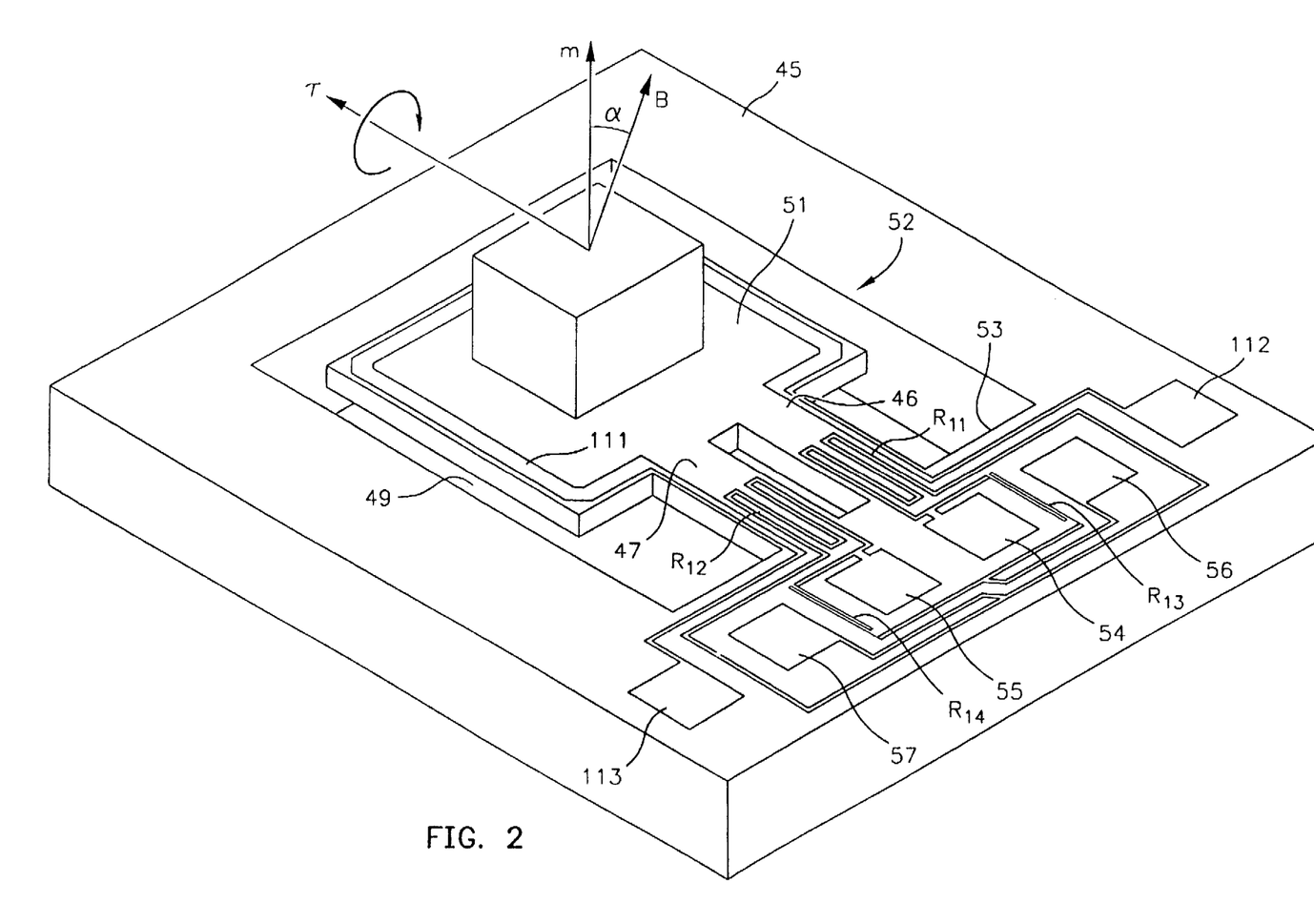
FIG. 2 is an isometric view of the torque lever chip of the present invention with a sample mounted on the platform of the torque lever showing the principle of measurement performed by the system of the invention.

FIG. 2 shows the torque magnetometer of the present invention. Substrate 45 is formed integrally with bridging or connecting legs 46 and 47 and platform 51, which combined comprise torque lever 52. Note that the torque lever is completely surrounded by the substrate material, preferably silicon, in a "pit" 49 in the substrate. This offers physical protection for the torque lever.

For reference purposes, torque lever 52 projects outwardly from edge 53 of the substrate by approximately 3 mm, with legs 46 and 47 being about 1 mm long, and platform 51 being about 2 mm square. The entire substrate is preferably a chip having dimensions of about 6×6×0.5 mm. The torque lever, which is cantilevered from edge 53 and is coplanar with the top surface of the substrate, has a thickness ranging from about 0.005 mm to about 0.05 mm. The thickness of the torque lever is directly related to the sensitivity of the instrument. For the highest sensitivity one would choose the magnetometer with a torque lever of about 0.005 mm thickness. The torque lever can accommodate samples up to at least about 0.01 gm, with typical sample dimensions not exceeding about 1.5×1.5×1.5 mm. The torque lever has a torque sensitivity of about $3\times10^{-10}$ Nm and corresponding to a moment sensitivity of approximately $2\times10^{-8}$ emu at 9T. These specifications are for reference purposes only and are not meant to be limiting or definitive.

The entire substrate is to be placed in a test chamber to accomplish testing of a sample. Deposited on the top surface of the substrate, by known means such as sputtering or evaporation, are all the circuit elements necessary to detect resistance changes due to bending or flexion.

Piezoresistors $R_{11}$ and $R_{12}$ are shown in serpentine form for enhanced sensitivity (there are four trace segments subject to bending or flexion) and are preferably made of constantan (typically about 60% copper and 40% nickel). These sensing resistors are deposited on legs 46 and 47. These piezoresistors change resistance with bending or flexion of the legs on which they are in surface bonded contact and thereby provide signals ($\Delta R$) which can be detected, compared and processed by any suitable means. A Wheatstone bridge is particularly useful because it very simply detects the $\Delta R$'s of resistors $R_{11}$ and $R_{12}$ and compares those changes so that the bridge output provides a direct indication of the direction and amount of bending or flexion which has occurred in legs 46 and 47 due to the applied magnetic field.

Bridge balancing resistors $R_{13}$ and $R_{14}$ are also shown as serpentine in shape, are deposited on the substrate body spaced from legs 46 and 47, and are not subject to the effects of bending or flexion of the torque lever legs. The balancing resistors are preferably also formed of constantan.

Contact pad 54 is deposited on the substrate and is connected between piezoresistance element $R_{11}$ and resistor $R_{13}$. Contact pad 55 is connected between piezoresistance element $R_{12}$ and resistor $R_{14}$. These are the signal detection pads, essentially where a signal detector, such as a volt meter, would be connected. While more sophisticated instrumentation could be employed as an indicator of the stresses to which the sample is subjected, a simple voltmeter, as indicated by the letter "V" in the drawing figures, is sufficient as an output indicator.

Figure 3:
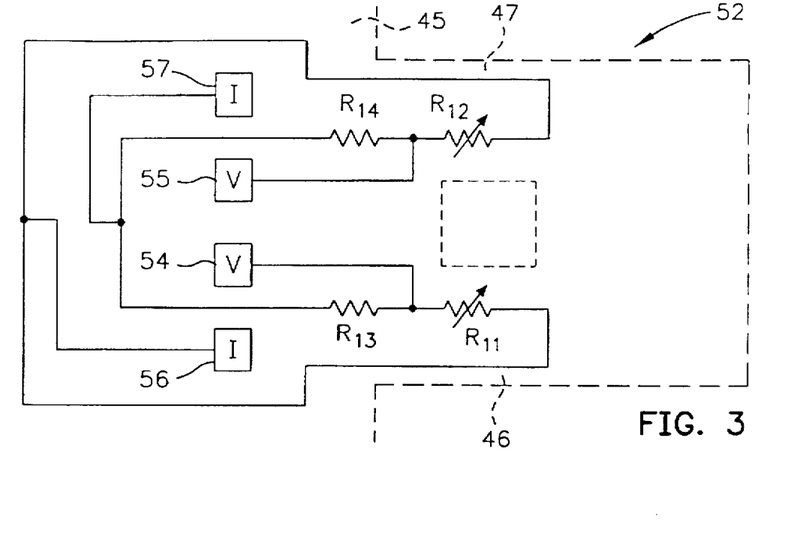
FIG. 3 is a schematic representation of the Wheatstone bridge shown in FIG. 2.

Contact pad 56 is connected between resistors $R_{13}$ and $R_{14}$ while contact pad 57 is connected between piezoresistors $R_{11}$ and $R_{12}$. Input power (typically a current of about 300 µA) is applied at those terminals by any appropriate conventional means (not shown). The complete Wheatstone bridge of the preferred embodiment of the present invention is shown in schematic form in FIG. 3. Note the inverted or inside-out arrangement compared with the standard schematic of FIG. 1 or FIG. 4B. While either bridge arrangement will provide satisfactory output signals, when the Hall effect is present or likely, the FIGS. 2 and 3 arrangement is preferably used to reduce or eliminate the Hall effect voltages.

Figure 5:
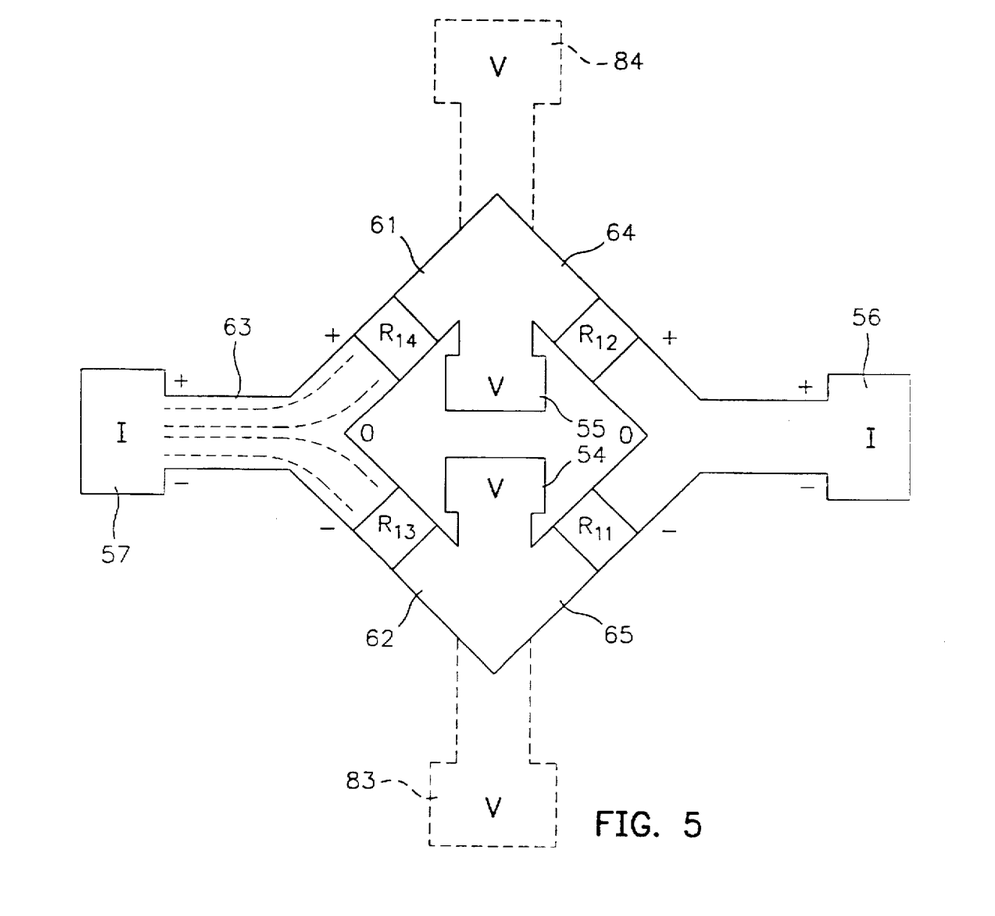
FIG. 5 is an enlarged view of the electrical traces showing the connections of FIG. 4.

The Hall effect and its control are further explained with reference to FIG. 5. This is a physical schematic representation of the bridge with the flat traces as deposited on the substrate shown exaggerated in width. In the presence of an external magnetic field an electrostatic potential will develop due to the Hall effect across traces 61, 62, 64 and 65, which are connected to and branch off from the signal input pads 56 and 57. This spurious potential will be greatest when the direction of the applied field is in the plane of circuit (torque-lever chip). Assuming for illustration purposes that the upper side of trace 63 develops a positive potential and that the lower side is negative as one would expect from the Hall effect, the edge of trace 61 opposite to the inside of the bridge would also be positive. The outside edge of trace 62 would be negative. That being so, the point at which trace 63 splits into traces 61 and 62 would define an equipotential neutral line across the circuit shown by "0." Furthermore, the entire inside perimeter connecting the two "0" points, as for example the points at which traces 62 and 65 meet and at which traces 61 and 64 meet, would remain at the same equipotential of zero even in the presence of an external magnetic field. It follows that correct measurement of the bridge balance or extent of unbalance, unaffected by an external magnetic field, is performed by sensing the voltage across the bridge from the points on the circuit that, branch off to the pads 55 and 54 (inside the bridge). On the other hand, it can be readily seen that measurements of the bridge balance performed by sensing the voltage across the bridge from the outside edges of the circuit where traces 61 and 64 meet and where traces 62 and 65 meet and branch off to pads 84 and 83 are subject to traditional spurious voltage potentials depending upon the magnitude and direction of the applied magnetic field.

It can be appreciated that any spurious voltage which could contaminate the very small signals from the piezoelectric resistance elements will not exist if the pick-up for the output signals is at a location at the intersection of two traces which is at zero voltage. This is true on the "inside" of the bridge traces, as shown in FIG. 5, whereas a potential other than zero exists on the outside of the traces. The Hall effect voltages are of microvolt level (peak to peak), but can literally be larger than the measurement signals from the piezoresistors.

Figure 4A:
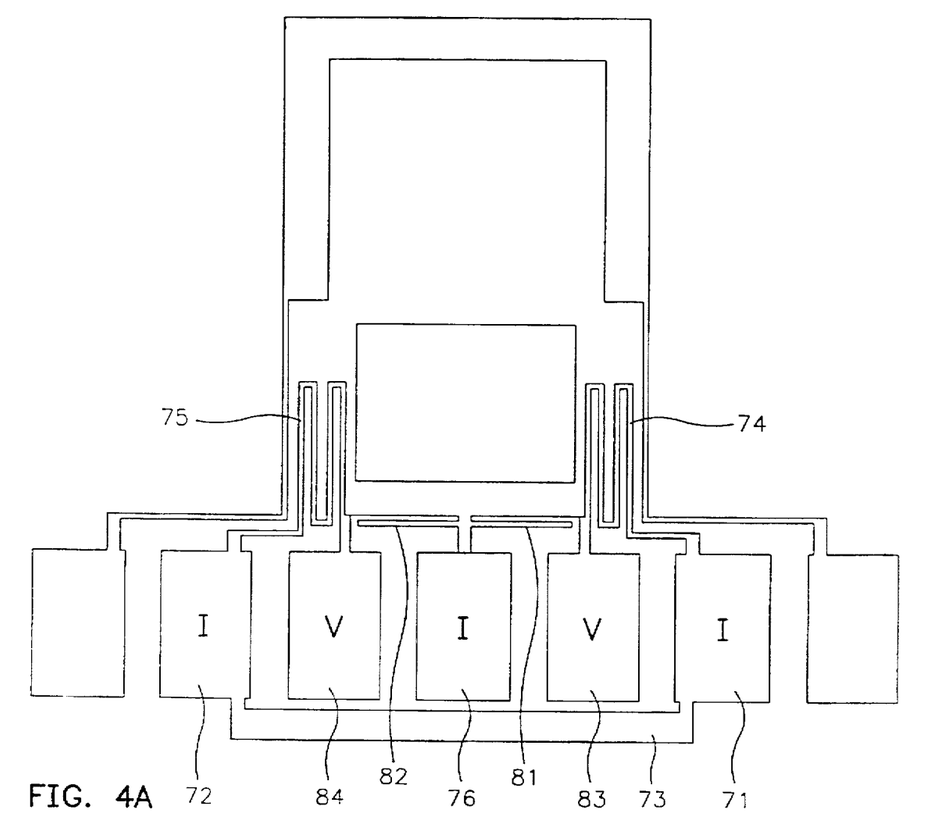
FIG. 4A is an alternative Wheatstone bridge configuration for use in the invention.
Figure 4B:
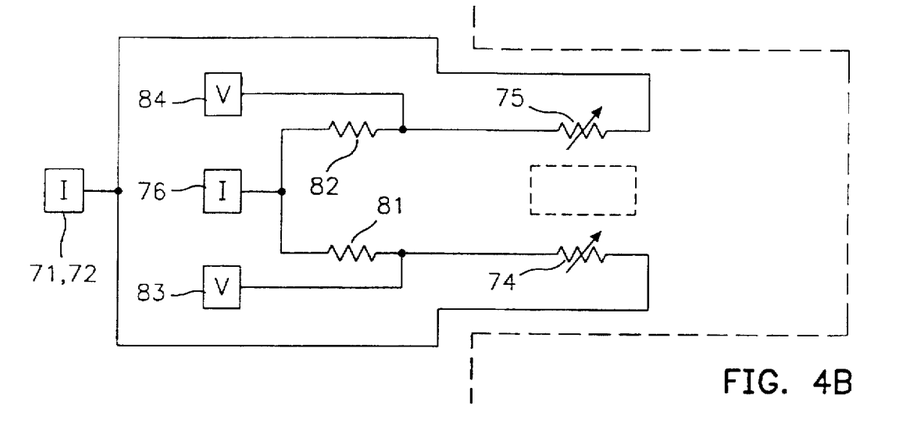
FIG. 4B is a schematic representation of the bridge of FIG. 4A.

The conventional bridge configuration is shown in FIG. 4A and 4B. Input signal pads 71 and 72 are shorted together by trace 73 and are connected between piezoresistance elements 74 and 75. Input signal pad 76 is connected between balancing resistor 81 and 82. Signal pick-up pad 83 is connected between piezoresistor 74 and resistor 81 while pick-up pad 84 is connected between piezoresistor 75 and resistor 82. While the schematic representation of FIG. 4B may not appear to have a significant difference from FIG. 3, the physical positioning of the connections of the contact pads to the traces as shown in FIG. 5 makes an important difference in the sensitivity of the magnetometer. Valuable output signals are available, even with relatively large applied magnetic fields. For typical test purposes, the applied magnetic field might range from −30 T to 30 T for a magnetometer having the size and characteristics previously specified as an example, although theoretically there is no limit. When the applied magnetic field exceeds about 1 T, the Hall effect voltages start to become significant and as the applied magnetic field increases, the accuracy and value of the torque magnetometer outputs diminish.

Figure 6:
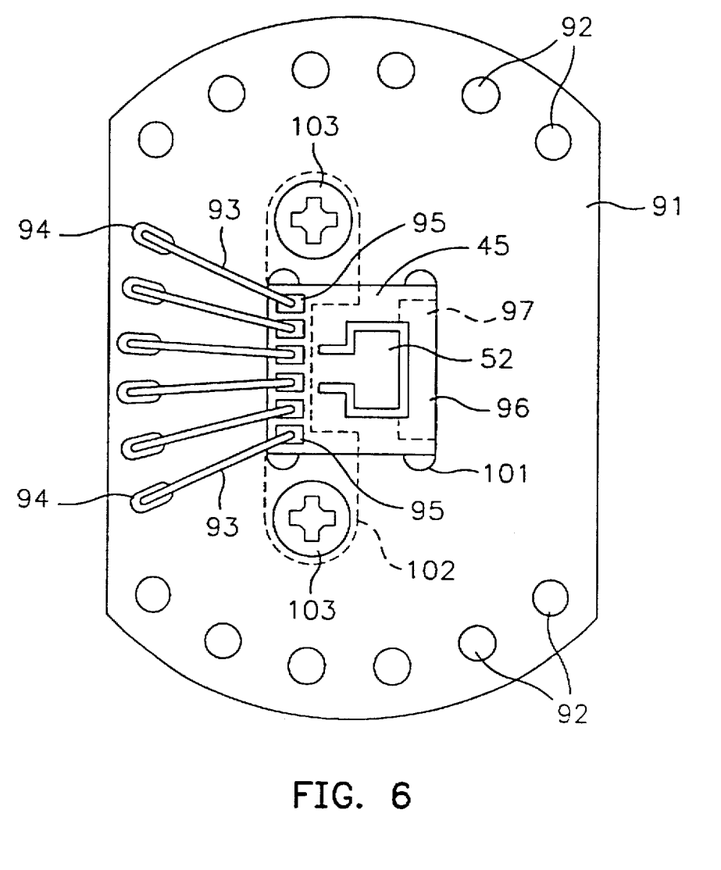
FIG. 6 is a top view of a modular chip board which plugs into a rotation platform for insertion into the test chamber.

A practical configuration of the invention is shown in FIG. 6. Chip board 91 is a modular carrier for torque magnetometer 52. The chip board has a plurality of pins 92 (only the heads of which are shown) which project downwardly, away from the visible surface of the chip board. The pins will enable the chip board to plug into the rotation platform of the test chamber.

Spring loaded contact fingers 93 are affixed to contact pads 94, with free ends 95 for making electrical contact with the bonding pads on torque magnetometer substrate 45. End 96 of the substrate rests on shoulder 97 in opening 101 in the chip board. Substrate 45 also rests on plate 102 removably secured across the side of opening 101 opposite to shoulder 97. The torque magnetometer is easily removed from chip board 91 by releasing securing means 103 so that plate 102 and magnetometer 52 can be removed through the bottom side of the chip board. Securing means 103 may be simple twist locks or other suitable elements.

The structure of FIG. 6 enables the magnetometer to be handled safely and in a modular manner, even after a sample has been loaded onto the paddle for testing. The chip board is adapted to receive torque magnetometers having different characteristics, or to replace damaged units. It further permits the magnetometer unit itself to be disposable since it is not permanently mounted in the test chamber. The plug-in aspect facilitates rapid change-over in the test chamber to enable tests to follow each other in relatively rapid succession. The known prior art employs hard wiring of the torque magnetometer to the substrate, thereby preventing any element of modularity. By contrast, the structure of the invention shown in FIG. 6 enables the torque magnetometer to be easily replaced and the magnetometer itself to be used in a variety of test chambers and apparatuses.

With reference again to FIG. 2, each embodiment of the torque magnetometer of the present invention includes calibration coil 111 with external connection contact or bonding pads 112 and 113. These are employed in the invention to establish initial set-up in full balance, taking into consideration all possible built-in causes for variations from one production magnetometer to another.

It is contemplated that the test chamber into which the torque magnetometer of the invention will be mounted has means for rotating the torque lever/substrate/sample in a fixed applied magnetic field; has means for rotating the applied magnetic field with the sample held stationary; and has means for varying the temperature to which the sample is subjected. The sample is secured to the torque lever paddle by any suitable adhesive, Apiezon wax being one example. With the modular configuration of FIG. 6, the sample can be deposited onto the paddle.

The torque lever of the invention has been shown as having two spaced parallel bridging legs. However, the invention can function without a space through the substrate between the surface areas on which the piezoresistances lie. The spaced legs are preferred for sensitivity purposes.

The torque magnetometer of the invention has many advantages over earlier such magnetometers. A very important factor is that it is of a practical, workable size. The relative dimensions of the invention and the known prior art are set out above. A key advantage is that with the entire sensing components (here the Wheatstone bridge) mounted on the substrate integral with the piezoresistors, all aspects of the sensing elements are subject to the same environmental changes. When that is coupled with the fact that the bridge balancing resistors are made from the same material as the piezoresistors, it is apparent that temperature changes, commonly a variable incorporated in the sample test procedures, do not have an unbalancing or decalibration effect. The resistors themselves are of metallic material, thereby being less subject to temperature induced stresses than would be vapor deposited resistors made from p-doped silicon, which is the typical material for piezoelectric resistors. With the torque magnetometer being formed in a pit in the substrate, physical protection is provided that was not previously available.

Because of its practical size and plug-in structure, the torque magnetometer of the invention can be handled safely. That is, it can be set up with a test sample in one place and moved to the test chamber without extreme fear of it being damaged.

Finally, with the reverse topology of the bridge connections, the potentially relatively large deleterious Hall effect voltages can be prevented from occurring.

In view of the above description, it is likely that modifications and improvements will occur to those skilled in the applicable technical field which are within the definitions of the claims. Therefore, the invention is to be limited only by the spirit and scope of the appended claims, when interpreted as broadly as permitted by the prior art.

What is claimed is:

1. A torque magnetometer for sensing the magnetic moment of a sample in the presence of an applied changing magnetic field in a test chamber, said magnetometer comprising:

an electrically non-conductive substrate formed with a cantilevered torque lever extending from one edge of said substrate, said substrate being configured to be removably mounted in the test chamber, said torque lever comprising:
a sample holding paddle distally projecting from said one edge; and
bridging means connecting said paddle to said one edge;

a pair of parallel spaced piezoresistors surface-mounted on said bridging means;

means on said substrate for detecting, comparing and processing signals from said piezoresistors indicative of resistance changes therein resulting from torsion on said paddle caused by magnetically induced torque on the sample to produce output signals representing the physical effect on the sample of the applied magnetic fields;

output terminals on said substrate for connecting said output signals to external signal processing circuitry; and input terminals on said substrate for applying electrical power to said piezoresistors.

2. The magnetometer recited in claim 1, wherein said substrate surrounds said paddle, said paddle being formed in a pit formed through said substrate.

3. The magnetometer recited in claim 1, wherein said signal detecting, comparing and processing means comprises a Wheatstone bridge, wherein said piezoresistors comprise two of the legs of said bridge.

4. The magnetometer recited in claim 3, wherein said bridge is formed entirely on said substrate and on said torque lever.

5. The magnetometer recited in claim 3, wherein said bridge comprises:

bridge balancing resistance elements formed on said substrate; and electrically conductive traces connecting said resistance elements and said piezoresistors so as to form four legs of said bridge, said traces having a predetermined width and, within the structure of said bridge, having inside edges and outside edges;

said output terminals being connected to said inside edges of said traces to thereby substantially eliminate Hall effect error signals.

6. The magnetometer recited in claim 1, wherein said piezoresistors are formed of constantan.

7. The magnetometer recited in claim 4, wherein all of the resistance elements of said Wheatstone bridge are formed of constantan.

8. The magnetometer recited in claim 1, wherein each said piezoresistor extends from said torque lever bridging means onto said substrate.

9. The magnetometer recited in claim 1, wherein said torque lever is coplaner with one surface of said substrate and is substantially thinner than said substrate.

10. The magnetometer recited in claim 9, wherein the thickness of said torque lever is at least an order of magnitude thinner than said substrate.

11. The magnetometer recited in claim 1, wherein said paddle is approximately square and is about 2 mm on a side, said paddle being spaced from said one edge of said substrate by about 1 mm, said torque lever being able to accommodate samples for test purposes having a mass equal to or less than about 0.01 gm and having dimensions as large as about 1.5×1.5×1.5 mm.

12. The magnetometer recited in claim 1, wherein said torque lever has a torque sensitivity of about $3 \times 10^{31 \, 10}$ Nm and a moment sensitivity of about $2 \times 10^{-8}$ emu at 9 T.

13. The magnetometer recited in claim 1, wherein said bridging means comprises a pair of spaced parallel legs.

14. The magnetometer recited in claim 5, wherein said bridge comprises two balancing resistors in two additional legs of said bridge, and wherein all four of said resistor elements are mounted on said substrate in a physically parallel arrangement with each other, thereby making all Hall effect voltages that develop to be substantially equivalent in all said resistor elements.

15. The magnetometer recited in claim 1, and further comprising:

a modular carrier board to which is removably mounted said substrate, said board having connection means for removably mounting said board in the test chamber, and contact elements for making connection to said input and output terminals of said substrate.

16. A torque magnetometer for sensing the magnetic moment of a sample in the presence of an applied changing magnetic field in a test chamber, said magnetometer comprising:

an electrically non-conductive substrate formed with a cantilevered torque lever extending from one edge of said substrate, said torque lever comprising:
a sample holding paddle distally projecting from said one edge; and
bridging means connecting said paddle to said one edge;

a pair of parallel spaced piezoresistors surface-mounted on said bridging means;

an electrical bridge configuration normally balanced when in the quiescent condition, said piezoresistors comprising two legs of said bridge configuration, said electrical bridge configuration having balancing resistance elements, and output terminals connected in said electrical bridge configuration for detecting an unbalance resulting from torsion on said paddle caused by magnetically induced torque on the sample, said balancing resistance elements being made of the same material as are said piezoresistors;

output terminals on said substrate for connecting said output signals to external signal processing circuitry; and input terminals on said substrate for applying electrical power to said piezoresistors.

17. The magnetometer recited in claim 16, wherein said bridge comprises:

electrically conductive traces connecting said bridge balance resistance elements and said piezoresistors so as to form four legs of said bridge, said traces having a predetermined width and, within the structure of said bridge, having inside edges and outside edges;

said output terminals being connected to said inside edges of said traces to thereby substantially eliminate Hall effect error signals.

18. The magnetometer recited in claim 16, wherein all of said piezoresistors and balancing resistor elements formed as traces of all-metallic material having a temperature coefficient of resistance substantially less than p-doped silicon piezoresistors.

19. The magnetometer recited in claim 16, wherein said output terminals are connected to the inside edges of said bridge traces to thereby substantially eliminate Hall effect error signals.

20. The magnetometer recited in claim 19, wherein said applied magnetic field in said test chamber is relatively large, being normally greater than about 1 T.

21. A torque magnetometer for sensing the magnetic moment of a sample in the presence of an applied changing magnetic field in a test chamber, said magnetometer comprising:

an electrically non-conductive substrate formed with a cantilevered torque lever extending from one edge of said substrate, said torque lever comprising:
a sample holding paddle distally projecting from said one edge; and
bridging means connecting said paddle to said one edge;

a pair of parallel spaced piezoresistors surface-mounted on said bridging means;

an electrical bridge configuration normally balanced when in the quiescent condition, said piezoresistors comprising two legs of said bridge configuration, said electrical bridge configuration having balancing resistance elements and output terminals connected in said electrical bridge configuration for detecting an unbalance resulting from torsion on said paddle caused by magnetically induced torque on the sample, said balancing resistance elements being made of the same material as are said piezoresistors;

output terminals on said substrate for connecting said output signals to external signal processing circuitry; and input terminals on said substrate for applying electrical power to said piezoresistors;

said bridge configuration further comprising electrically conductive traces connecting said balancing resistance elements and said piezoresistors on said substrate so as to form four legs of said bridge, said traces having a predetermined width and, within the structure of said bridge, having inside edges and outside edges;

said output terminals being connected to said inside edges of said traces to thereby substantially eliminate Hall effect error signals that occur at magnetic fields greater than about 1 T.

22. The magnetometer recited in claim 21, wherein said piezoresistors and said balancing resistor elements are formed of the same all-metallic material.

23. The magnetometer recited in claim 22, wherein said resistance elements are formed of constantan.

24. The magnetometer recited in claim 23, wherein said output terminals are connected to voltage sensing points on the inside edges of said traces which are at equal potential.

25. A method for sensing the magnetic moment of a sample in the presence of an applied changing magnetic field in a test chamber, said method comprising the steps of:

forming an electrically non-conductive substrate with a cantilevered torque lever extending from one edge of the substrate and configured with a paddle on which the sample to be tested is retained, the paddle being connected to the substrate by bridging means;

forming a pair of parallel spaced piezoresistors on the surface of the bridging means and extending onto the substrate;

forming an electrical balancing bridge configuration on the substrate, the piezoresistors being two legs of the bridge, there being two other balancing resistance element legs of the bridge;

forming output terminals on the substrate which are connected in the bridge to sense unbalance conditions, the output terminals being configured to connect signals indicative of the state of balance and unbalance of the bridge to external signal processing circuitry;

forming input terminals on the substrate configured to apply electrical power to the piezoresistors;

mounting the substrate with a rotation platform within the test chamber;

applying a magnetic field to the sample on the paddle in the test chamber;

varying the strength of the magnetic field; and rotating the platform while applying the magnetic field to the sample in the test chamber.

26. The method recited in claim 25, wherein the piezoresistors, the balancing resistance elements and the output terminals are formed on the substrate.

27. The method recited in claim 25, wherein the output terminals are connected to the inside of the traces forming the bridge to thereby substantially eliminate Hall effect error signals.

* * * * *